(12) United States Patent
Srinivasan et al.

(10) Patent No.: US 9,881,511 B1
(45) Date of Patent: Jan. 30, 2018

(54) MONITORING AND MOTIVATING HEALTH HABITS

(71) Applicant: Intel Corporation, Santa Clara, CA (US)

(72) Inventors: Bharadwaj Srinivasan, San Francisco, CA (US); Aaron Samuel Filner, San Francisco, CA (US); Kathleen Elizabeth Linn, San Francisco, CA (US); Konstantine M. Pangalos, Oakland, CA (US); Mac Baker, San Francisco, CA (US); Julie Wilner, San Francisco, CA (US)

(73) Assignee: Intel Corporation, Santa Clara, CA (US)

( * ) Notice: Subject to any disclaimer, the term of this patent is extended or adjusted under 35 U.S.C. 154(b) by 695 days.

(21) Appl. No.: 14/082,055

(22) Filed: Nov. 15, 2013

Related U.S. Application Data

(60) Provisional application No. 61/727,070, filed on Nov. 15, 2012.

(51) Int. Cl.
*G09B 5/02* (2006.01)

(52) U.S. Cl.
CPC .................................. *G09B 5/02* (2013.01)

(58) Field of Classification Search
CPC ........................................................ G09B 5/02
USPC ......................................................... 434/262
See application file for complete search history.

(56) References Cited

U.S. PATENT DOCUMENTS

| | | | |
|---|---|---|---|
| 8,475,367 B1* | 7/2013 | Yuen | G06F 19/3418 128/920 |
| 2007/0072156 A1* | 3/2007 | Kaufman | G09B 19/0092 434/236 |
| 2007/0100595 A1* | 5/2007 | Earles | G06Q 30/02 703/13 |
| 2014/0045156 A1* | 2/2014 | Alessandri | G09B 19/0092 434/236 |

* cited by examiner

*Primary Examiner* — Thomas Hong
(74) *Attorney, Agent, or Firm* — Patent Capital Group (57) ABSTRACT

A system and a method are disclosed for analyzing health-related data associated with a user and suggesting goals to the user to improve health. The system and method monitor progress towards the goal.

12 Claims, 7 Drawing Sheets

| Name | Action | Relevance | Example Daily Goal | Trigger |
|---|---|---|---|---|
| Consistent Bed Time | Schedule and commit to a regular bedtime. | A consistent bedtime reinforces the body's sleep-wake cycle. Go to bed at the same time every day, including weekends. | Go to sleep within 15 minutes of 10:30pm | The time at which a user falls asleep exhibits a standard deviation of more than 15 hours per week |
| Regular Rising | Plan and commit to a regular wake-up time. | It is beneficial to maintain regular periods of wakefulness and sleep. | Wake up within 15 minutes of 7:30am | The time at which a user wakes up exhibits a standard deviation of more than 15 hours per week |
| Steps | Take a minimum number of steps per day | Maintaining activity is a critical element of health. | Take at least 7000 steps | The user takes less than an average of 7000 steps/day in a calendar week. |
| Evening stroll | Take a stroll in the evening | Walking is one of the easiest ways to stay fit. Start with new ritual of evening walks. | Take 2000 steps between 6pm and 10 pm | User logs less than 2000 steps between 6pm and 10pm, local time |
| Afternoon Stoll | Take a stroll in the afternoon | Walking is one of the easiest ways to stay fit. Start with new ritual of afternoon walks. | Take3000 steps bet 12pm and 5pm | User logs less than 3000 steps between 12pm and 5pm local time. |
| Morning Stroll | Take a stroll in the morning | Walking is one of the easiest ways to stay fit. Start with new ritual of morning walks. | Take 1000 steps between 6am and 10am | User logs less than 5000 steps between 6am and 10am, local time. |
| Wear | Schedule and commit to a regular bedtime. | Wear a sensor device to learn more about your activity and sleep | Wear the sensing device for at least 20 hours | User wears the data collection device for an average of less than 20 hours per day |
| Sleep more hours | Sleep for a specified number of hours or more. | Getting enough sleep is a critical factor in maintaining ones health | Sleep for within 30 minutes of 8 hours | User's total sleep duration averages less than 7 or more than 9 hours |
| Minutes of activity | Get your activity level up to a brisk walk or higher. | It is recommended to perform 30 minutes of moderate aerobic activity to maintain health. | Perform 30 minutes or more of moderate activity | User averages less than 30 minutes per day of activity |
| Burn more calories | Get more active during the day to burn a specific number of calories | Burning more calories, combined with a healthy diet can contribute to weight loss and help ensure that you have a minimum amount of total activity in your day. | Burn 2500 calories or more | User averages less than 2500 calories burned each day over a calendar week |
| Reduce 'max inactive time' | Go no more than your target number of minutes without getting up and moving | Sitting for too long slows your caloric burn and sitting for too many hours in the day has been linked with increased cardiovascular disease. | Make sure to perform any physical activity at least once every 60 minutes while awake | User is inactive for periods of 60 minutes or more, an average of more than once per week |

MONITORING AND MOTIVATING HEALTH HABITS

CROSS REFERENCE TO RELATED APPLICATIONS

This application claims the benefit of U.S. Provisional Application No. 61/727,070, filed Nov. 15, 2012, which is incorporated by reference in its entirety.

BACKGROUND

1. Field of Art

The disclosure generally relates to the field of motivating healthy habits in users of a wearable device that monitors physical parameters.

2. Description of the Related Art

Lifestyle choices such as the frequency of physical activity and duration of sleep can have significant and lasting implications on overall health. Behaviors that have small negative impacts on health, when repeated regularly over time, can result in more serious health conditions than any one instance of these behaviors could have caused. It is the cumulative impact of these adverse behaviors that is most easily prevented by intervention to remove them from the daily routine. Removing or replacing these adverse behaviors from the daily routine represents the easiest way to prevent future health conditions. Similarly, behaviors that have small positive impacts on health, when repeated regularly over time, can result in the prevention of serious health conditions and significant improvements to quality of life. Repeated behaviors, whether beneficial or detrimental, are referred to as "habits". The term "health-related habits" refers to any habits that have an impact on health over time.

Software systems have, to date, relied heavily on explicit user input in the form of self-reporting. Users often cease to use such systems after a short amount of time, since the continual effort of manual logging becomes a tiresome burden. Once the initial excitement and curiosity of such a system subsides, users are likely to stop using the system within a matter of days or weeks. This rapid drop in adherence means that any potential health benefits of such systems are typically never achieved. This is largely due to the fact that establishing lasting health-related habits takes a month or more.

BRIEF DESCRIPTION OF DRAWINGS

The disclosed embodiments have other advantages and features which will be more readily apparent from the detailed description, the appended claims, and the accompanying figures (or drawings). A brief introduction of the figures is below.

FIG. 5 illustrates a table of exemplary habits.

DETAILED DESCRIPTION

The Figures (FIGS.) and the following description relate to preferred embodiments by way of illustration only. It should be noted that from the following discussion, alternative embodiments of the structures and methods disclosed herein will be readily recognized as viable alternatives that may be employed without departing from the principles of what is claimed.

Reference will now be made in detail to several embodiments, examples of which are illustrated in the accompanying figures. It is noted that wherever practicable similar or like reference numbers may be used in the figures and may indicate similar or like functionality. The figures depict embodiments of the disclosed system (or method) for purposes of illustration only. One skilled in the art will readily recognize from the following description that alternative embodiments of the structures and methods illustrated herein may be employed without departing from the principles described herein.

Configuration Overview

One embodiment of a disclosed system, method and computer readable storage medium for monitoring health-related parameters and assist in the development of positive health-related habits. A device worn by the user or placed in proximity to the user measures various parameters. The parameters are analyzed to identify possible habits that a user could adopt to improve health. Adopted habits are monitored and a user is presented with progress towards the successful adoption of the habit. These represent a significant advancement over any system that relies more heavily on manual user input. Automatic tracking results in a higher rate and duration of user adherence and thus more successfully promote the development and maintenance of health-related habits.

Exemplary Architectural Overview

Figure 1:
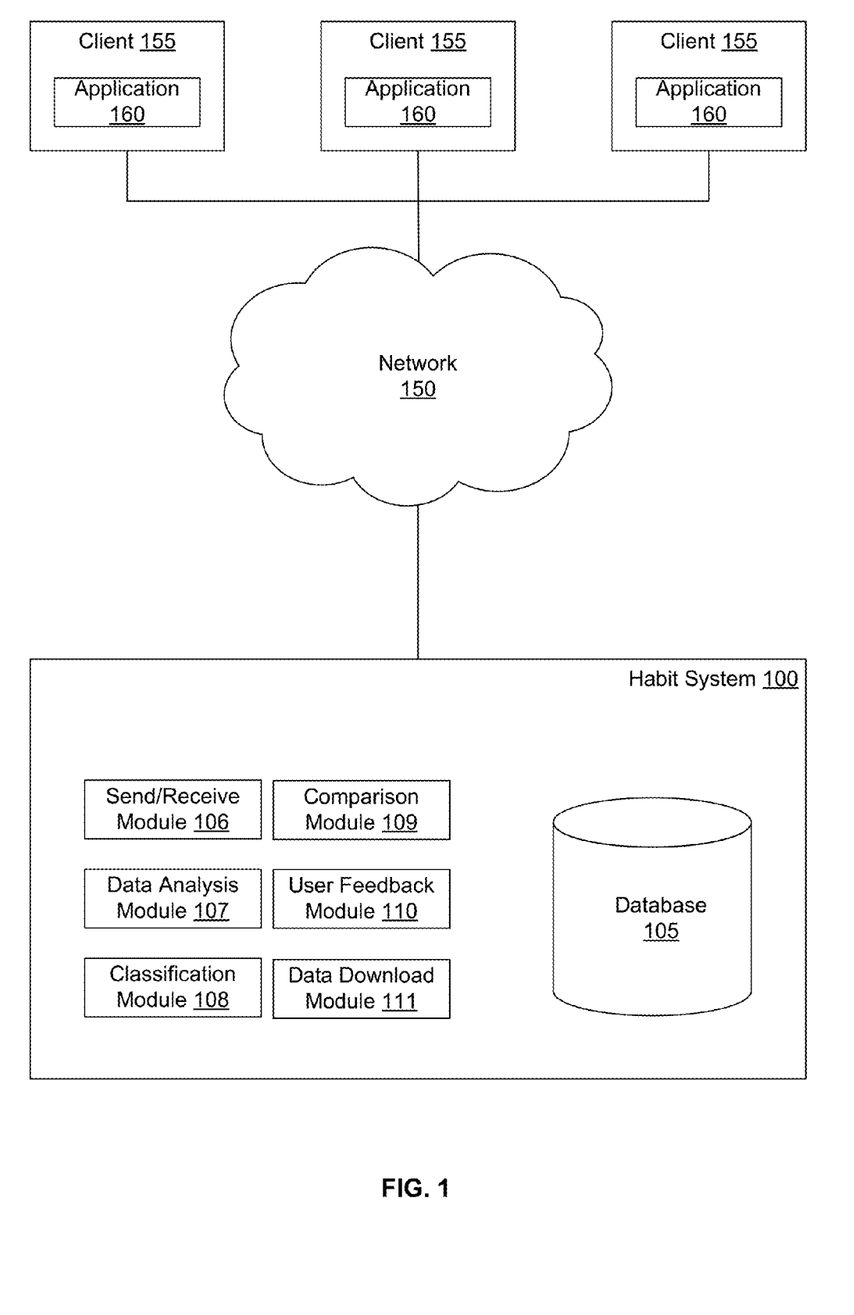
FIG. 1 illustrates one embodiment of a system architecture for encouraging health habits for users.

Referring now to FIG. 1, it illustrates an embodiment of a system architecture of a system for encouraging health habits for users. The habit system 100 comprises a send/receive module 106, data analysis module 107, classification module 108, comparison module 109, user feedback module 110, data download module 111 and a database 105. For simplicity only one send/receive module 106, data analysis module 107, classification module 108, comparison module 109, user feedback module 110, data download module 111 and database 105 are shown but in practice many of each of these components may be in operation.

It is noted that habit system 100 may also refer to a configuration having more than one physical computer, each of which is communicatively coupled together to form a logical computer configuration. The computers themselves may have generally high performance CPUs, with 1 G or more of memory, and 100 G or more of disk storage. Of course, other types of computers can be used, and it is expected that as more powerful computers are developed in the future, they can be configured in accordance with the teachings here. The functionality implemented by any of the elements can be provided from computer program products that are stored in tangible computer readable storage mediums (e.g., RAM, hard disk, or optical/magnetic media), or by equivalent implementations in hardware and/or firmware.

As is known in the art, the habit system 100 is adapted to execute computer program engines (or modules) for providing functionality described herein. As used herein, the term "module" refers to computer program logic utilized to provide the specified functionality. Thus, module can be implemented in hardware, firmware, and/or software. Firmware or software configurations comprise program code (or instructions) that can be stored on a non-transitory computer readable storage medium and executable by one or more processors (generally, processor). In one embodiment, program engines, such as send/receive module 106, data analysis module 107, classification module 108, comparison module 109, user feedback module 110 and data download module 111, are stored at the habit system 100, loaded into the memory and executed by the processor.

Embodiments of the entities described herein can include other and/or different modules than the ones described here. In addition, the functionality attributed to the modules can be performed by other or different modules in other embodiments. Moreover, this description occasionally omits the term "module" for purposes of clarity and convenience.

Send/receive module 103 receives data from the client 155 and provides feedback to the client 155 generated by the user feedback module 110. The data analysis module 107 analyzes data received by the send/receive module 106. Examples of analysis performed by the data analysis module 107 includes parsing, interpreting, aligning, aggregating and decrypting data received, as required for further processing. The classification module 108 interprets the analyzed data generated by the data analysis module 107 generating classifications of events, states and detections represented by data from the one or more clients 155. The comparison module 109 compares analyzed data to historical data, data from other users, benchmarks, recommendations, averages or guidelines. User feedback module 110 generates user feedback for the user which is provided by the data download module 111 to the client 155. The database 105 stores data utilized in the operation of the other modules of the habit system 100. Operation of the modules of habit system 100 are described in greater detail in reference to the exemplary process overview described below.

The client 155 can be any type of computing device that is adapted to access the habit system 100 over the network 150. Examples of clients 155 include, but are not limited to, health monitoring devices (e.g., wearable devices and scales), portable computing devices such as laptops, tablet computers, smartphones, etc. Clients 155 additionally include desktop computers. Some clients 155, such as wearable devices, portable computers and smartphones, include functionalities for obtaining health data. Application 160 at the client 155 is a user interface allowing access by the user to the functionality of the client 155 and access to the habit system 100. In some embodiments, application 160 is a browser application.

The network 150 through which the client 155 communicates with other clients 155 and habit system 100 can be any type of network, wired or wireless, known in the art. Examples include the Internet, but may also be any network, including but not limited to a LAN, a MAN, a WAN, an 802.11 network, an 802.16 network, a mobile, wired or wireless network, telecommunication network, a private network, or a virtual private network, and any combination thereof. The network 150 may also refer to an ad-hoc networked connection, examples of which include Bluetooth, Bluetooth Low Energy, Zigbee, Near Field Communication (NFC), or infrared communications.

Exemplary Device Overview

Figure 2:
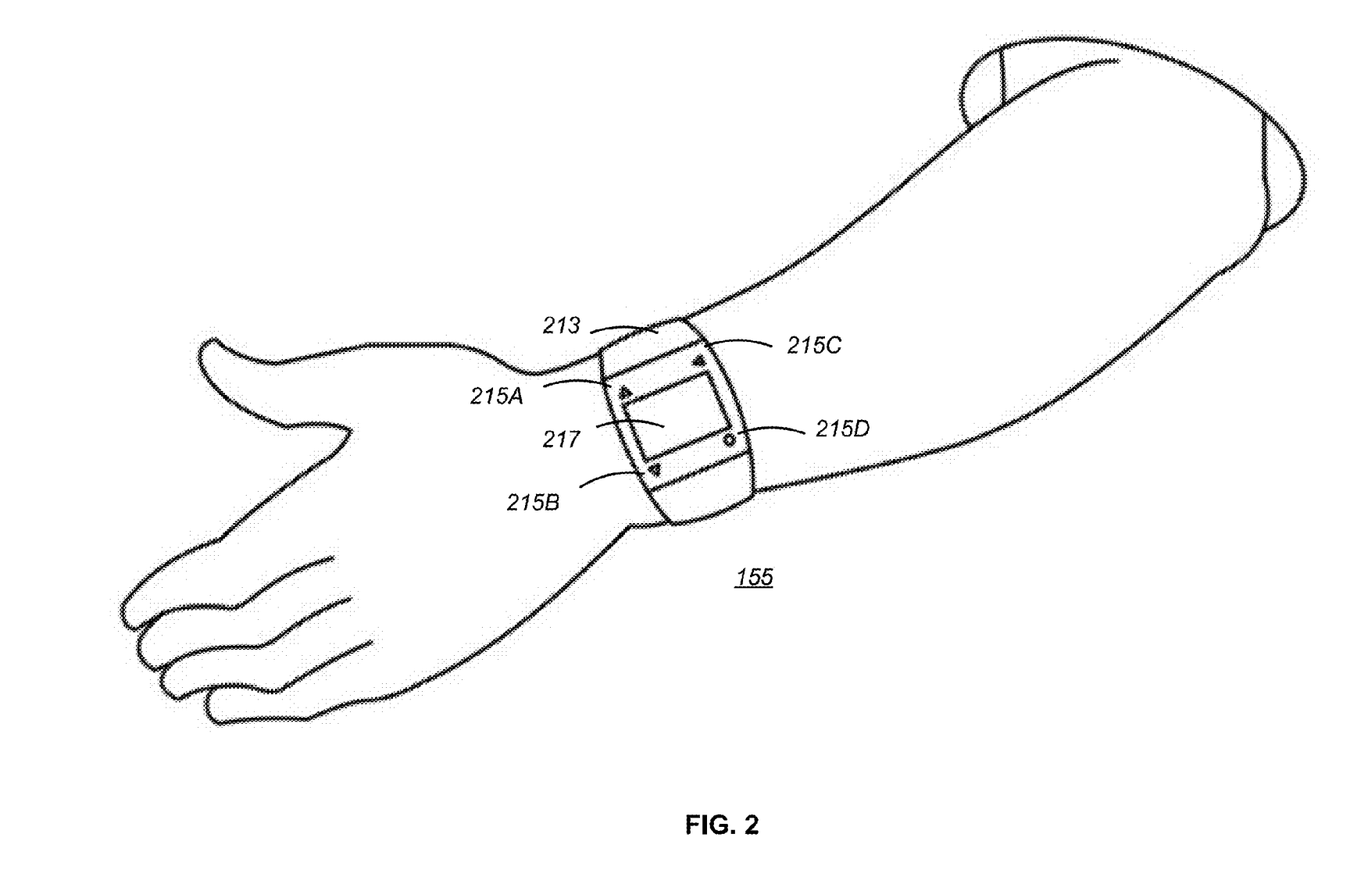
FIG. 2 illustrates an example wearable device client.

FIG. 2 illustrates an example wearable device client 155 which is configured to be in close proximity to or in contact with a user. For example, the client 155 may be worn on a user's appendage (e.g., an arm, a wrist, an ankle) or portion thereof. In one embodiment, the wearable client 155 is a physiological monitoring device for monitoring activities of its wearer and calculating various physiological and kinematic parameters, such as activity levels, caloric expenditure, step counts, heart-rate, body temperature, perspiration, and sleep patterns. In some embodiments, a user can manually provide information manually to the client 155 which in turn is used by the client 155 in calculating parameters. Additionally the client 155 measures environmental parameters such as humidity and ambient temperature. A fastening system 213 fastens the client 155 to a user's appendage. The fastening system 213 may be removable, exchangeable, or customizable. One example fastening system 213 includes a band around the user's appendage held in place through a buckle, a clasp, a hook, a pin, Velcro, elastic compression, or magnets. Furthermore, although embodiments are described herein with respect to a wrist-worn device client 155, other form factors or designed wear locations of the client 155 may alternatively be used. For example, embodiments of the method described herein may be implemented in arm-worn devices, head-worn devices, clip-on devices, and so forth.

The exemplary client 155 includes a display 217 and several user interaction points 215A, 215B, 215C, 215D. The display 217 and user interaction points 215 may be separate components of the client 155, or may be a single component. For example, the display 217 may be a touch-sensitive display configured to receive user touch inputs and display information to the user. Embodiments of the display 217 include a liquid crystal display (LCD), a light-emitting diode (LED) display, and an organic LED display. In an embodiment, the display 217 shows information to a user such as biometric data measured by sensors. Embodiments of the interaction points 215 include buttons, dials, and capacitive sensors.

Figure 3:
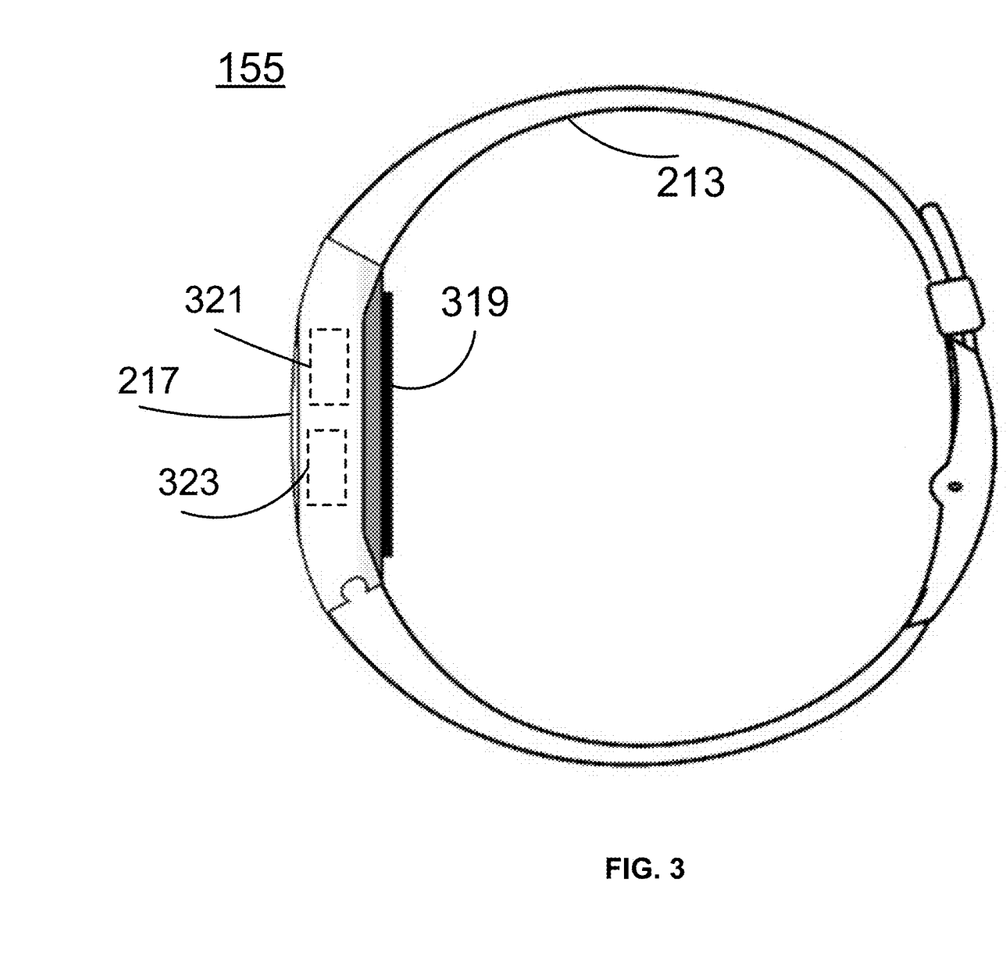
FIG. 3 illustrates a side view of an embodiment of the exemplary wearable client.

FIG. 3 illustrates a side view of an embodiment of the exemplary wearable client 155, showing the fastening system 213, the display 217, a sensor panel 319, a processor 321, and a memory 323. The sensor panel 319 comprises one or more sensors for monitoring user physiological or kinematic parameters or ambient conditions. In one embodiment, the sensor panel 319 includes sensors for measuring blood flow, device motion, perspiration, or temperature. The client 155 can measure both ambient temperature as well as the skin temperature of the user wearing the client 155. The sensor panel is communicatively coupled to the processor 321 and/or memory 323. The processor 321 executes instructions, prepares data for display, and/or processes sensor data. Embodiments of the processor 321 include a microprocessor, a central processing unit (CPU), a graphics processing unit (GPU), a digital signal processor (DSP), one or more application specific integrated circuits (ASICs), one or more field programmable gate arrays (FPGAs), one or more programmable logic devices (PLDs), or any combination of these. The memory 323 stores data collected from the sensor panel 319 and stores instructions for execution by the processor 321. Embodiments of the memory include flash memory, random-access memory (RAM), read-only memory (ROM), or a combination thereof. The memory 323 includes a machine-readable medium on which are stored instructions (e.g., software) embodying any one or more of the methodologies or functions described herein. The instructions may also reside, completely or at least partially, within the processor 321 (e.g., within a processor's cache memory) during execution thereof. In an embodiment, the functionality of the processor 321, memory 323, and other components is provided by a component such as a microcontroller.

It should be noted that client 155 may include additional components. In an embodiment, the client 155 includes vibratory motors, electroactive polymers, or piezoelectric surfaces for haptic feedback. The client 155 may include network interface devices such as a universal serial bus (USB) port or wireless transceivers for communication using protocols such as WiFi, Bluetooth, Bluetooth Low Energy (BTLE), Adaptive Network Topology (ANT), and Zigbee. In an embodiment the client 155 may be connected (e.g., networked) to other machines including to additional clients 155. In one embodiment, the wearable device client 155 communicates to a second client 155, such as a laptop computer, smartphone, tablet computer, etc. In some embodiments, the second client 155 further communicates with a remotely located habit system 100. In a networked deployment, the wearable device client 155 may operate in the capacity of a client machine in a server-client network environment for example where the habit system 100 is a server, or as a peer machine in a peer-to-peer (or distributed) network environment.

In an embodiment, the client 155 includes a power supply such as a battery, a motion-powered generator, or a solar generator. Embodiments may include an audio signaling device or additional visual indicators such as LEDs for providing feedback to a user. Embodiments may include electronic filters, amplifiers, power source regulators, analog to digital converters (ADC), digital to analog converters (DAC), and other circuitry.

The client 155 may include a motion sensor for detecting, quantifying and characterizing the motion of the client 155, and thus the user who is carrying or wearing the client 155. Example motion sensors include accelerometers, gyroscopes, pressure sensors, compasses, global positioning systems, magnetometers and combinations thereof. Data from the motion sensor can be used by the processor in many ways including counting steps taken by the user and estimating calories burned. This information can in turn be used by the processor 321 to provide feedback to the user on progress towards goals for daily levels of activity and calorie usage.

The client 155 may include a heart rate sensor. In one embodiment, heart rate is determined through an optical sensor. One or more optical emitters on the sensor panel 319 emits light into and onto the skin of the wearer. Example optical emitters include light emitting diodes (LEDs) and lasers. In some embodiments light emitted from the optical emitter(s) 407 is in the visible yellow and green ranges (500-600 nm). In other embodiments light in the visible spectrum, such as blue and red, or the infrared spectrum may be used instead of or in addition to green light. The optical emitter(s) optionally additionally emit light at wavelengths other than that used to measure heart rate. A portion of the light is absorbed by the tissue and blood of the user. A portion of the light is reflected back to the sensor 319 where it is detected by an optical detector. The processor 321 receives data from the optical detector and determines from it various features of the user's blood flow, including heart rate. The processor 321 can use this information to determine not just heart rate but the user's stress state.

The client 155 may include functionality for logging activities such as tracking food and beverages consumed by the user which can then be used to determine caloric intake. Other activity logging includes reminders to take medication and the ability to confirm that the medication has been taken.

The user can enter the information via the application 160 at the client 155. If the client 155 is a wearable device like the example in FIG. 2, information can be entered via user interaction points 215 or the display 217. If the client 155 is a laptop, tablet, smartphone or other computing device, the information can be entered using the means conventionally associated with those devices for entry of information by the user.

Exemplary Process Overview

Referring now to FIGS. 4-7, illustrated is an exemplary process for monitoring health and suggesting and motivating health-improving habits. Behaviors that are well-suited for use with the disclosed system and method are those that can be tracked without input from the user and can be performed by most people and do not require extensive training although configurations that allow for addition of user input (e.g., caloric intake related information) may be incorporated. Habits include those that promote a health activity as well as those that discourage unhealthy activities. Exemplary habits that improve health include taking a certain number of steps (e.g., 10,000) each day, a certain number of steps (e.g., 1,000) during a break time (e.g., meal break), going to sleep at a consistent time each evening, waking up at a consistent time each morning, getting sufficient sleep (e.g., between 6 and 9 hours) each night, etc.

Figure 4:
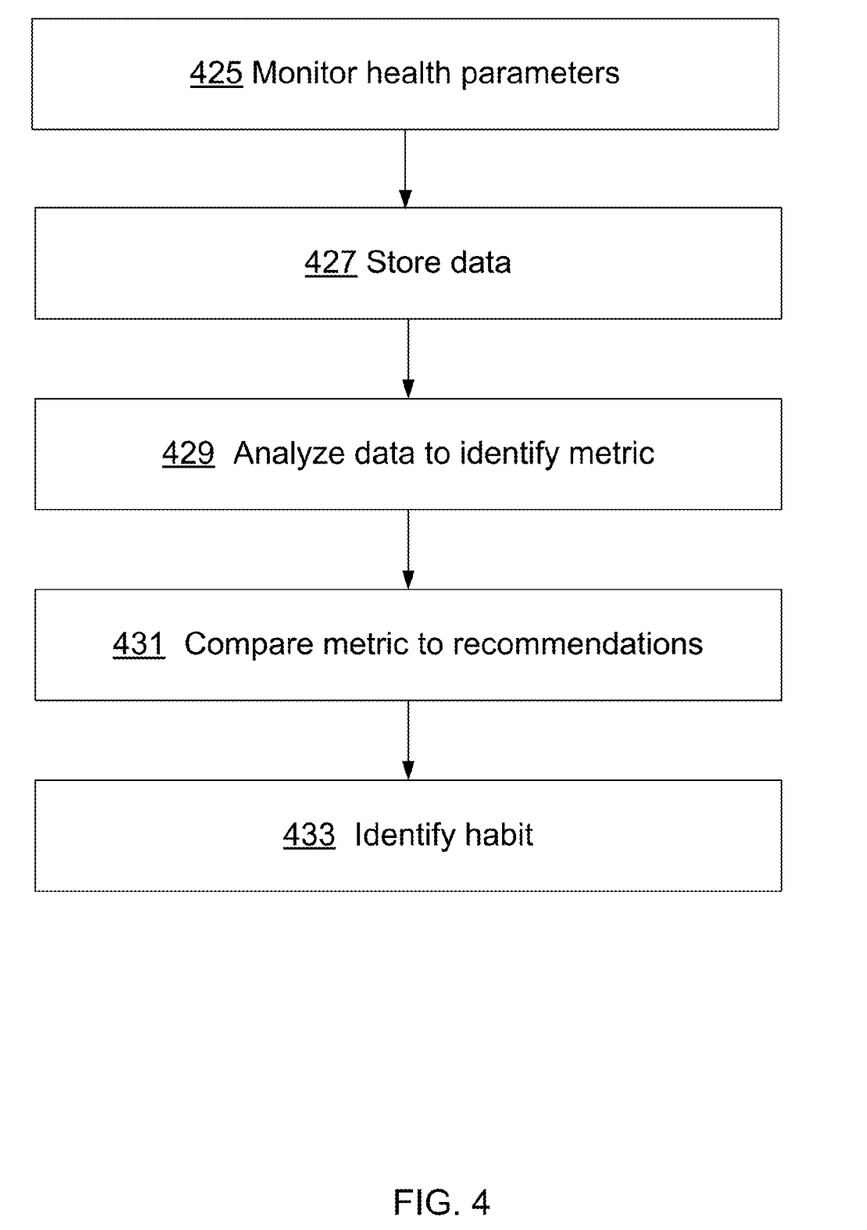
FIG. 4 illustrates a flowchart of an exemplary method for suggesting a habit to a user.

FIG. 4 illustrates a flow chart of an exemplary method for suggesting a habit to a user. In the example process, a user is wearing a wearable client 155. The client 155 includes sensors that monitor 425 various health parameters including a user's motion and blood flow. This information is received at the send/receive module 106 of the habit system 100 and stored 427 at the database 105. Periodically, the data analysis module 107 retrieves the stored data and analyzes 429 it to identify metrics. In one example the metric is number of steps taken and the analyzed data is motion data. When analyzing whether a user is asleep or awake, the data analysis module 107 analyzes motion data and blood flow data to identify wakefulness vs sleep. The analyzed data are stored in the database 105 for purposes of comparison with new data in the future. In some embodiments, the metrics are identified by analyzing information provided by the user in addition to data collected automatically by sensors in wearable client 155.

The comparison module 109 compares 431 the determined data against recommendation for that parameter for healthy individuals. In the example of determining a number of steps taken in a day, the steps per day are compared against recommendations for numbers of steps taken in a day by healthy individuals. In some embodiments, the database 105 includes demographic information about the user and the comparison module 109 compares 431 the determined number of steps to more personalized recommendations based on the user's demographic information.

Based on the comparison made by the comparison module 109, user feedback module 110 identifies 433 a habit to suggest to the user. For example, if the recommendation is that individuals take 10,000 steps a day and the user took only 3,000 steps a day during the measured period, the user feedback module 110 identifies 433 10,000 steps a day as a habit for the user to work on. This habit is provided to the user via the send/receive module 106. In some embodiments, the user feedback module 110 provides a more personalized habit to the user. In the above example, the user is currently rather far from the recommended 10,000 steps per day. The user feedback module 110 could identify 433 instead an intermediate goal between 3,000 and 10,000 steps a day. The user feedback module 110 could be programmed to identify 333 a habit that is no more than threshold percentage higher than the user's current status in that parameter. For example, 10% more steps than the user currently takes would be 3,300 steps per day. In yet another alternative, the user feedback module 110 identifies that a user would benefit by taking more steps per day and the user provides the target set of steps to take per day as the goal for the habit.

If a user decides to adopt the suggestion and work towards developing the suggested habit, the habit is stored as associated with the user in the database 105.

Other habits can also be implemented using the disclosed system and method. The wearable client 155 can be used to analyze a user's stress level and thus habits to reduce stress, such as scheduled breathing exercises, stretching, desk yoga, can also be implemented. The table at FIG. 5 provides additional example habits to be suggested to the user as well as the measured parameter that triggers the suggestion of the habit by the user feedback module 110.

The suggestion of the habit can be made to the user visually at any type of client 155. If the client 155 is a wearable device, it could be shown at display 217. Additionally or alternatively, the suggested habit could be shown via an application 160 at a client 155. The habit system 100 could email the user with the suggested habit or send a text message. In addition to the habit suggestion, the send/receive module 106 can provide for display data related to the suggested habit. In the above steps per day example, the number of steps taken per day for a day or multiple days in the past can be displayed to the user.

In an alternate embodiment, the user requests from the habit system 100 suggestions for habits to improve an area of health. In such an embodiment, the habit system categorizes habits. Example categories include improving fitness and increasing productivity. Example improving fitness habits include increasing the number of steps taken in a day. In response to the request the habit system 100 proceeds according to steps 429, 431 and 433 in FIG. 4 to identify habits based on the user's data. The user feedback module 110 provides the identified habits to the user via the send/receive module 106. The user's selection of one or more habits at client 155 is received back at the habit system 100 and stored in the database 105.

Figure 6:
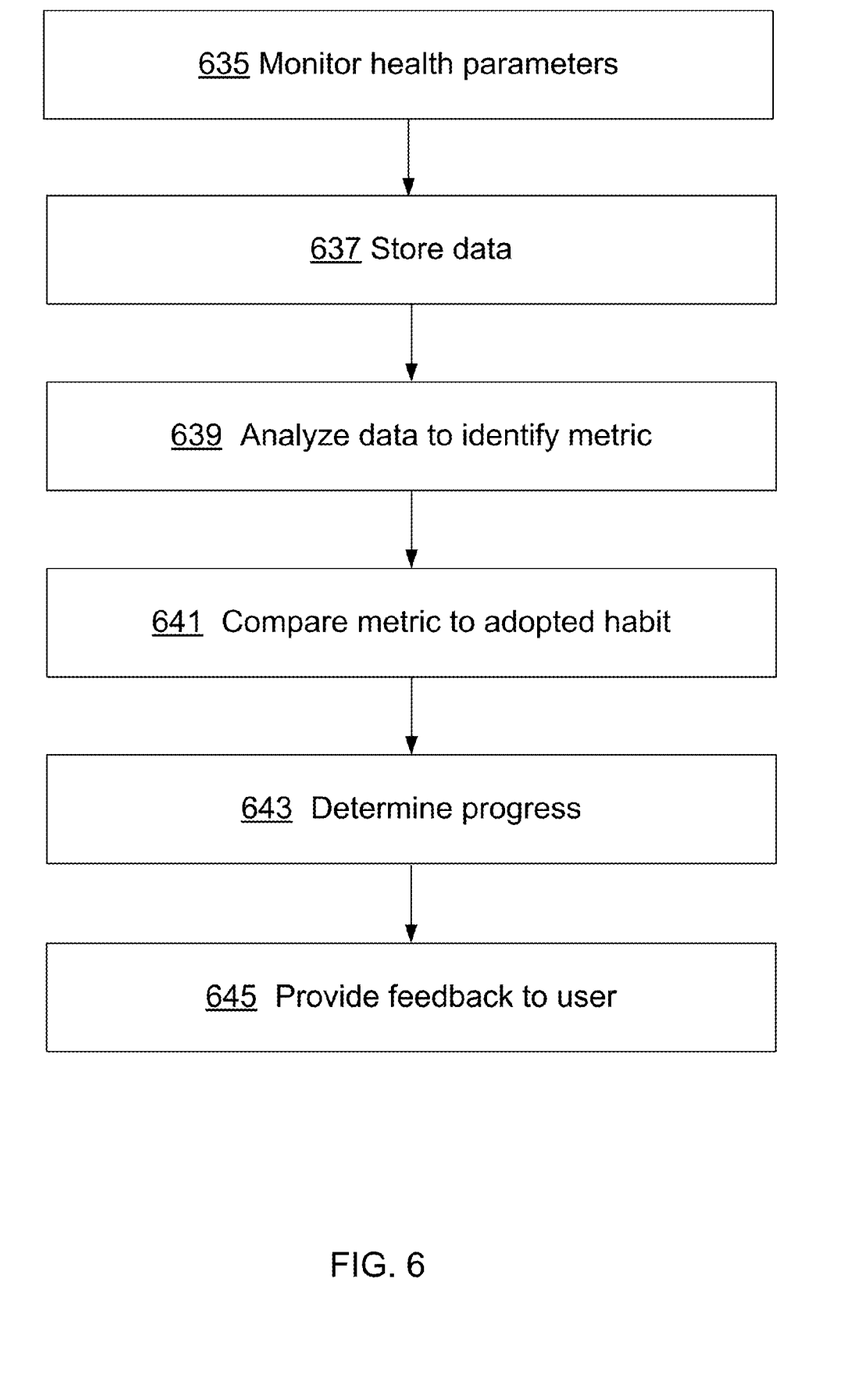
FIG. 6 illustrates a flowchart for monitoring an adopted habit.

FIG. 6 illustrates a flowchart for monitoring an adopted habit. The first three steps are similar to those for identifying a habit. Sensors at the client 155 monitor 625 the parameter related to the adopted habit. If the habit involves a number of steps to take each day, the sensor is the motion sensor. The motion data is received at the send/receive module 106 at the habit system 100 and stored 627 at the database 105. The data analysis module 107 analyzes 329 the data to identify the number of steps taken in the measured time period. This information is stored in database 105. Periodically, the comparison module 109 compares 641 the stored number of steps taken by a user against the stored habit and determines 643 the user's progress towards successful adoption of the habit. Responsive to how the user is doing, the user feedback module 110 provides 645 feedback to the user. If the user is missing the set goal by larger than a threshold, the user feedback module 110 can reduce the goal for the habit. Returning to the habit of taking 3,300 steps per day, if the user is making only 3,100 steps per day, the user feedback module 110 could modify the goal to 3,150 steps per day. Alternatively, the user feedback module 110 could modify the goal to making 3,300 steps per day for fewer days per week. Having a user achieve a goal is important even if it is achieved more slowly because if a user gets frustrated at not achieving a goal, the user is likely to abandon the attempt and then health is not improved.

Figure 7:
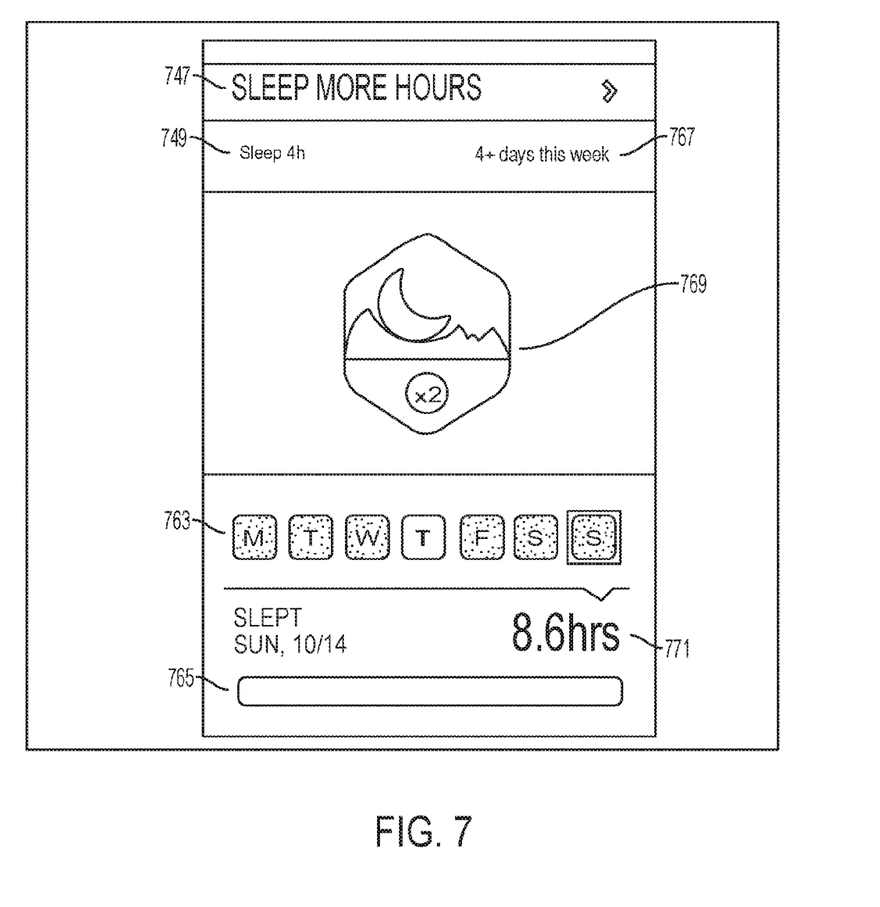
FIG. 7 illustrates a user interface demonstrating progress towards a habit.

FIG. 7 is an illustration of a user interface demonstrating progress towards a habit. The habit name 747 is "Sleep More Hours." The habit requirements 749 are sleeping four hours every day. The goal 767 number of days to accomplish the habit in a week is four. A calendar bar 763 demonstrates the days on which the habit was met: Monday, Tuesday, Wednesday, Friday, Saturday and Sunday. The habit was not met on Thursday. The outline around Sunday indicates that the day on which the display is viewed is Sunday. Status bar 765 shows that the habit was met the most recent night. If the user had only slept two hours the prior night, the bar would be half-filled. The graphic 769 illustrates that the most recent night of sleep was twice the habit and number 771 provides a text output of the number of hours slept. In some embodiments, the display of feedback to the user emphasizes a trend in the user's progress towards successfully adopting the habit and less on whether the habit was met on any one day.

The update displayed to the user can include both processed data (e.g., the number of hours slept or steps taken) and unprocessed data (e.g., a temperature). Processed data includes data that is determined using information from more than sensor and/or contextual information.

In another embodiment, the user has successfully adopted the previously suggested habit or achieved the habit for a threshold number of weeks (e.g., four weeks). The user feedback module 110 suggests one or more additional habits to the user based on other determined metrics for the user. A new habit may be a new target for a previous habit. If for example a user has successfully been taking an average of 5,000 steps per day, the new habit may be to take an average of 10,000 per day.

In some embodiments, the habit system 100 recommends only one habit at a time for users who are new to the habit system 100 and then increases to more habits at one time as users have been using the habit system 100 longer. Optionally, a user's success at achieving habits is also a factor in determining how many habits to suggest to a user at one time. For example, a user may have been a user of the habit system 100 for a relatively long time but the user takes a long time to adopt a habit. The habit system 100 would not suggest the user take on more than one habit at a time.

In another embodiment, the user chooses a level of achievement in the habit appropriate to their abilities and desires. This level may be constrained to levels that are known to relate to positive health-related behavior, or may be unconstrained. That level of achievement is either attained or missed each day. In this embodiment, the initial goal is to perform each actively monitored habit once (for any one day) out of a calendar week (7 days). This initial goal may also be set to twice (any two days) in the calendar week. An example benefit of this strategy is to make the achievement of a successful week reasonable when a habit is new to a user. Establishing early success is an important part of starting to develop a health-related habit. Similarly, for habits that have a range of difficulty options available, users can choose the level of attainment. For example, if a user is known to be inactive at the time of joining the system, setting a daily step count goal lower than for a user with a more active lifestyle is appropriate. For example, a user with a more sedentary lifestyle may set an initial goal of 5000 steps for a successful day, whereas a more active user may set this goal to 15000 steps.

Additional Considerations

In some embodiments, the habit system 100 provides tips for users to help them achieve selected habits. These tips may be provided to the user throughout the adoption of a habit and/or increased in frequency if the user is not making progress towards adopting the habit. The habit system 100 can monitor the progress of users in combination with the tips provided to those users to determine the relative efficacy of the various tips.

Additionally or alternatively the habit system 100 provides encouragement to the user. Encouragement can take various forms including messages to the user with information about the health benefits that can be gained through mastering the habit. Encouragement can also include rewards such as points which can be redeemed for merchandise, gift cards and the like. Points can be awarded based on the difficulty of the habit.

In some embodiments, some or all of the functions of the habit system 100 are performed locally at the client 155. For example, client 155 can include a data analysis module 107, comparison module 109, classification module 108, user feedback module 111 and a database 105. This is useful because presentation to the user is not dependent on the availability of a remotely located habit system 100.

Alternatively, the client device 155 capturing the health-related data may transmit this to another wearable or portable client device 155 for processing. For example, a wearable client device 155 may transmit health-related data to a smartphone client 155, which processes the data locally and displays feedback to the user. In such an embodiment, the smartphone client includes a data analysis module 107, comparison module 109, classification module 108, user feedback module 111 and a database 105. This is useful because a user is relatively likely to be carrying a smartphone. The smartphone however is likely to have more capacity for storage and processing than the wearable device 155.

Health-related data may be combined with contextual data from the smartphone including multimedia information like photos and videos, geographic location, environmental data such as weather, ambient light level, temperature, or social information such as friendships or proximity to others. Ambient light measurements can be analyzed by the processor 321 to identify amounts of UV light in the ambient light. This is useful to keep track of a user's exposure to possibly harmful components of light. Information about the user's environment can also be determined by using location information from a GPS system to look up various publicly available environment conditions at that location like smog and pollen counts.

In some embodiments, the habit system 100 combines health data with information from the user's calendar. Other contextual information includes check ins at locations via a social networking application 160 at the client 155. The habit system 100 uses this information to provide context for habits and tips. For example, if a user is trying to increase the number of calories burned but is frequently "checking in" at a fast food restaurant, the habit system 100 might suggest that the user's increased calorie burn would have a larger effect if the user reduced the number of meals at the fast food restaurant. A user's social activities as assessed via social networking activity are also used by the processor 321 as a proxy for the user's emotional health. Contextual information can be provided from any device which can communicate via a network. For example, the habit system 100 can use information from a "smart" home system if the user provides the habit system 100 access to the "smart" home system. "Smart" home systems include information about whether appliances in the home are on or off. Information about televisions, lights, computers being on can be used to assess a user's sleep, for example.

The disclosed system and methods are an improvement over existing methods as the habit system 100 can identify habits that would potentially be useful to a user by analyzing and determining health-related parameters of the user. Monitoring of the habit can be accomplished automatically and results provided to the user automatically. Thus even if a user is not particularly motivated on a given day and would otherwise not enter manual information if the system required manual entry of information for tracking, with the disclosed system and method, the user's progress continues to be tracked.

Some portions of above description describe the embodiments in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. It should be understood that these terms are not intended as synonyms for each other. For example, some embodiments may be described using the term "connected" to indicate that two or more elements are in direct physical or electrical contact with each other. In another example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the invention. This description should be read to include one or at least one and the singular also includes the plural unless it is obvious that it is meant otherwise.

The features and advantages described in the specification are not all inclusive and, in particular, many additional features and advantages will be apparent to one of ordinary skill in the art in view of the drawings, specification, and claims. Moreover, it should be noted that the language used in the specification has been principally selected for readability and instructional purposes, and may not have been selected to delineate or circumscribe the disclosed subject matter.

Upon reading this disclosure, those of skill in the art will appreciate still additional alternative structural and functional designs for a system and a process for assessing a user's health habits and suggesting new habits through the disclosed principles herein. Thus, while particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

What is claimed is:

1. A computer-implemented method for encouraging health-related habits comprising:
   receiving from at least one sensor comprising at least one of a motion sensor and an optical heart rate sensor health-related data associated with a user, wherein the health related data includes at least one of the user's movement and blood flow as measured by the at least one sensor and wherein the at least one sensor is incorporated into a device worn by the user;
   determining by one or more processors incorporated into the device a health-related goal based on the received health-related data, the determining comprising:
      comparing the received health-related data with a recommendation for a particular parameter, wherein the recommendation is based on demographic information of the user; and
      based on the comparing, identifying the health-related goal to suggest to the user;
   providing the health-related goal to the user by displaying the health related goal on a display incorporated into the device;
   receiving data associated with the health-related goal, wherein the data associated with the health-related goal includes contextual information associated with the user comprising at least one of geographic location, weather, ambient light level, temperature, and social network data;
   determining progress towards the health-related goal by the one or more processors based on the received data associated with the health-related goal; and
   providing the user a reward comprising several points for progress toward the health-related goal, wherein the number of points is proportional to a difficulty of the health related goal;
   responsive to determining completion of the health-related goal:
      comparing additional health-related data associated with the user received from the at least one sensor subsequent to the previous identifying to the particular parameter;
      based on the comparing, identifying a second health-related goal to suggest to the user, wherein second health related goal is identified based on a proximity of the additional health-related data for the particular parameter to the recommendation and at least one of an age and gender of the user.

2. The method of claim 1 wherein determining the second health-related goal comprises identifying the second health-related goal based on the first health-related goal.

3. The method of claim 1 wherein determining the second health-related goal comprises+identifying the second health-related goal based on the first health-related goal and the additional health-related data.

4. The method of claim 1 wherein the reward comprises points that are redeemable by the user for at least one of merchandise, services, and gift cards.

5. A system for encouraging health-related habits comprising a processor configured to:
   receive from at least one sensor comprising at least one of a motion sensor and an optical heart rate sensor health-related data associated with a user, wherein the health related data includes at least one of the user's movement and blood flow as measured by the at least one sensor and wherein the at least one sensor is incorporated into a device worn by the user;
   determine by one or more processors incorporated into the device a health-related goal based on the received health-related data, the determining comprising:
      comparing the received health-related data with a recommendation for a particular parameter, wherein the recommendation is based on demographic information of the user; and
      based on the comparing, identifying the health-related goal to suggest to the user;
   provide the health-related goal to the user by displaying the health related goal on a display incorporated into the device;
   receive data associated with the health-related goal, wherein the data associated with the health-related goal includes contextual information associated with the user comprising at least one of geographic location, weather, ambient light level, temperature, and social network data;
   determine progress towards the health-related goal by the one or more processors based on the received data associated with the health-related goal; and
   provide the user a reward comprising several points for progress toward the health-related goal, wherein the number of points is proportional to a difficulty of the health related goal;
   responsive to determining completion of the health-related goal:
      compare additional health-related data associated with the user received from the at least one sensor subsequent to the previous identifying to the particular parameter;
      based on the comparing, identify a second health-related goal to suggest to the user, wherein second health related goal is identified based on a proximity of the additional health-related data for the particular parameter to the recommendation and at least one of an age and gender of the user.

6. The system of claim 5 wherein determining the second health-related goal comprises identifying the second health-related goal based on the first health-related goal.

7. The system of claim 5 wherein determining the second health-related goal comprises+identifying the second health-related goal based on the first health-related goal and the additional health-related data.

8. The system of claim 5 wherein the reward comprises points that are redeemable by the user for at least one of merchandise, services, and gift cards.

9. A non-transitory computer readable medium configured to store instructions, the instructions when executed by a processor cause the processor to:
receive from at least one sensor comprising at least one of a motion sensor and an optical heart rate sensor health-related data associated with a user, wherein the health related data includes at least one of the user's movement and blood flow as measured by the at least one sensor and wherein the at least one sensor is incorporated into a device worn by the user;
determine by one or more processors incorporated into the device a health-related goal based on the received health-related data, the determining comprising:
comparing the received health-related data with a recommendation for a particular parameter, wherein the recommendation is based on demographic information of the user; and
based on the comparing, identifying the health-related goal to suggest to the user;
provide the health-related goal to the user by displaying the health related goal on a display incorporated into the device;
receive data associated with the health-related goal, wherein the data associated with the health-related goal includes contextual information associated with the user comprising at least one of geographic location, weather, ambient light level, temperature, and social network data;
determine progress towards the health-related goal by the one or more processors based on the received data associated with the health-related goal; and
provide the user a reward comprising several points for progress toward the health-related goal, wherein the number of points is proportional to a difficulty of the health related goal;
responsive to determining completion of the health-related goal:
compare additional health-related data associated with the user received from the at least one sensor subsequent to the previous identifying to the particular parameter;
based on the comparing, identify a second health-related goal to suggest to the user, wherein second health related goal is identified based on a proximity of the additional health-related data for the particular parameter to the recommendation and at least one of an age and gender of the user.

10. The computer readable medium of claim 9 wherein instructions for identifying the second health-related goal comprise instructions for determining the second health-related goal based on the first health-related goal.

11. The computer readable medium of claim 9 wherein instructions for determining the second health-related goal comprise instructions identifying the second health-related goal based on the first health-related goal and the additional health-related data.

12. The computer readable medium of claim 9 wherein the reward comprises points that are redeemable by the user for at least one of merchandise, services, and gift cards.

* * * * *

UNITED STATES PATENT AND TRADEMARK OFFICE
CERTIFICATE OF CORRECTION

PATENT NO. : 9,881,511 B1
APPLICATION NO. : 14/082055
DATED : January 30, 2018
INVENTOR(S) : Bharadwaj Srinivasan et al.

It is certified that error appears in the above-identified patent and that said Letters Patent is hereby corrected as shown below:

In the Drawings

On sheet 5 of 7, in FIG. 5, Line 31, delete "bum" and insert -- burn --, therefor.

In the Claims

In Column 12, Line 11, in Claim 3, delete "comprises+identifying" and insert -- comprises identifying --, therefor.

In Column 12, Line 67, in Claim 7, delete "comprises+identifying" and insert -- comprises identifying --, therefor.

Signed and Sealed this
Tenth Day of April, 2018

Andrei Iancu
*Director of the United States Patent and Trademark Office*